United States Patent [19]
Song et al.

[11] Patent Number: 5,792,955
[45] Date of Patent: Aug. 11, 1998

[54] APPARATUS FOR MEASURING A LOSS OF SOUND TRAVELED IN A MUFFLER OF AN AUTOMOBILE

[75] Inventors: Jin-Ho Song; Hong-Jun Mun; Choi-Ki Song, all of Kyoungki-Do, Rep. of Korea

[73] Assignee: Kia Motors Corporation, Seoul, Rep. of Korea

[21] Appl. No.: 697,148

[22] Filed: Aug. 20, 1996

[30] Foreign Application Priority Data

Jul. 12, 1996 [KR] Rep. of Korea .................. 96-28115

[51] Int. Cl.⁶ .................................................. G01N 29/20
[52] U.S. Cl. .......................................... 73/646; 73/584
[58] Field of Search ............................ 73/646, 658, 584, 73/592, DIG. 1, 865.8, 865.9, 116, 117

[56] References Cited

U.S. PATENT DOCUMENTS 4,676,111   6/1987   Wagner ........................... 73/646

Primary Examiner—Christine K. Oda

[57] ABSTRACT

An apparatus for measuring loss of sound traveled in a muffler of an automobile comprises: a first and second pipe between which the muffler, to be tested, is inserted; a sound source connected to one end of the first pipe opposite to the muffler to create a sound into the first and second pipes; the first microphones mounted at the first pipe to measure the level of sound before the muffler; the second microphones mounted at the second pipe to measure the level of sound after the muffler; and a non-reflect means connected to the second pipe for the sound passing through the first and second pipes so as not to reflect into them.

7 Claims, 4 Drawing Sheets

APPARATUS FOR MEASURING A LOSS OF SOUND TRAVELED IN A MUFFLER OF AN AUTOMOBILE

FIELD OF THE INVENTION

The present invention relates to apparatus for measuring a loss of sound traveled in a muffler of an automobile and more particularly, for measuring a flow rate passing through the muffler or a loss of sound traveled therein.

PRIOR ART

In general, in order to operate an engine of an automobile, an air-fuel mixture is inducted into the cylinder of engine and burned or combusted therein. Afterwards, the residual gas or exhaust after combustion is exhausted to the out of the automobile. The exhaust apparatus for emitting the residual gas out of the automobile includes: an exhaust manifold for collecting the burn gas from each cylinder; a catalytic converter for purifying the burn gas; an exhaust pipe for guiding the burn gas to the outer; and a muffler.

In the meanwhile, a bellows is mounted at the forward portion of the exhaust pipe to absorb vibration treated from running automobile and from the power stroke of engine.

As described in more detailed, the exhaust apparatus is divided into five portions: a forward portion of the exhaust pipe connected to the exhaust manifold and having a vibration absorbing bellows; a catalytic converter connected to the forward of the exhaust pipe; an auxiliary muffler connected to the catalytic converter; a main muffler connected to the auxiliary muffler; and a baffle connected to the main muffler.

The coupling portion of the exhaust pipe is bolted to the exhaust manifold of engine. The bellows is mounted at the middle portion of the exhaust pipe to efficiently absorb the vibration transmitted from the exhaust manifold to the lower end of the automobile through the exhaust apparatus.

The other end of the forward pipe is connected to the catalytic converter so that the catalytic converter may purify exhaust gas. The auxiliary muffler connected to the catalytic converter reduces the noise created in exhaustion and the main muffler additionally reduces the noise processed by the auxiliary muffler. Finally, the exhaust gas passes through the above components from the engine and leaves the automobile by the baffle.

As mentioned above, the muffler of automobile not only purifies the exhaust gas but reduces the noise created in exhaust.

Therefore, the muffler is tested for exhaust gas purification and noise reduction before mounted at the automobile and thereafter it is mounted. One known noise testing method is to indicate the ratio of sound pressure for sound pressure value passing through the muffler to the sound pressure value inputted in the muffler. Other various testing methods have been effected.

The conventional apparatus for measuring the loss of sound traveled in a muffler, however, is complex in structure and the obtained value is incorrect so when the muffler is mounted at automobile, the noise created at exhaustion is not reduced as a satisfactory value.

SUMMARY OF THE INVENTION

Therefore, the purpose of the present invention is to provide apparatus for measuring correctly the loss of noise passing through the muffler using a simpler method that efficiently reduces the noise.

To achieve the above purpose, an apparatus for measuring loss of sound traveled in a muffler of an automobile comprises: a first and second pipe between which the muffler, to be tested, is inserted; a sound source connected to one end of the first pipe opposite to the muffler to create a sound into the first and second pipes; the first microphones mounted at the first pipe to measure the level of sound before the muffler; the second microphones mounted at the second pipe to measure the level of sound after the muffler; and a non-reflect means connected to the second pipe for the sound passing through the first and second pipes so as not to reflect into them.

The apparatus for measuring loss of sound traveled in a muffler of an automobile further comprises a flow creating device for providing an air flow in the first pipe thereby aiding for the sound generated from the sound source to travel into the first and second pipes.

According to the present invention, the microphone is located at a distance from the end of the pipe connected to the muffler and an additional microphone is located at the above distance from the previously mounted microphone.

According to the present invention, each of the microphones is inserted into a jig fastened to a screw hole formed at the first and second pipes.

According to the present invention, the non-reflect device has an enlarged end and a sound absorber filled in the inner of the enlarged end to prevent sound reflecting.

According to the present invention, the flow creating device comprises a fan operated by a motor, a guide pipe connected to the first pipe to guide the air flow created by the fan to the first pipe, a fan muffler provided at the middle portion of the guide pipe to eliminate the noise created by the operation of the fan and a flow rate sensor. The sound source is received preferably into a insulating chamber so that an external noise can be insulated.

In accordance with the apparatus for measuring loss of sound traveled in a muffler of an automobile as mentioned above, the levels of sound before and after the muffler can be accurately measured so a loss of sound passing through the muffler is measured thereby obtaining the muffler of automobile of good sound eliminating ability.

BRIEF DESCRIPTION OF DRAWINGS

These and other features, aspects, and advantages of the present invention will become better understood with regard to the following description, appended claims, and accompanying drawings wherein:

DETAILED DESCRIPTION

Figure 1A:
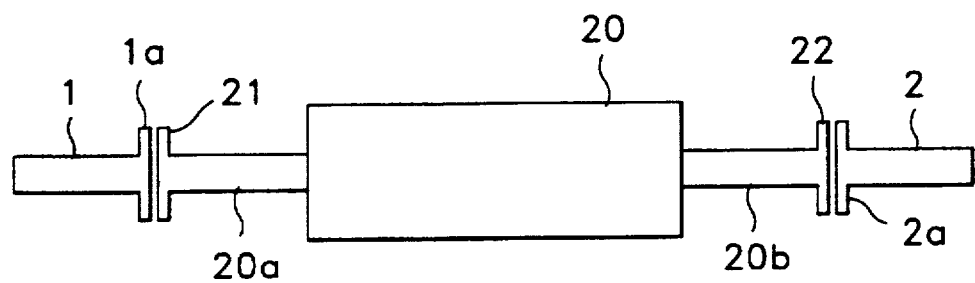
FIG. 1A is a schematic view of the muffler to be tested.
Figure 1B:
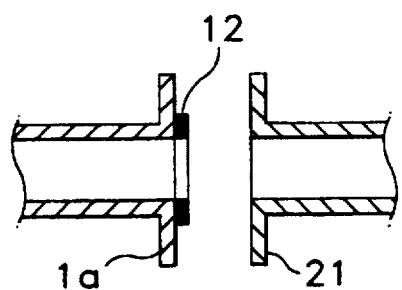
FIG. 1B shows the connecting portion of the muffler of FIG. 1 and the apparatus for measuring loss of sound traveled in a muffler of an automobile according to the present invention.
Figure 1C:
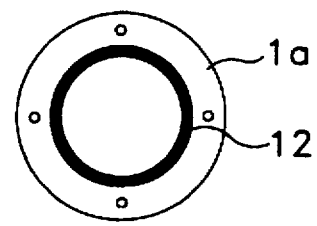
FIG. 1C is a front view of the rubber pad inserted into the connecting portion of FIG. 1B.

FIG. 1A is a schematic view of the muffler to be tested, FIG. 1B showing the connecting portion of the muffler of FIG. 1 and the apparatus for measuring a loss of the sound traveled in a muffler of an automobile according to the present invention and FIG. 1C being a front view of the rubber pad inserted into the connecting portion of FIG. 1B.

As shown in FIG. 1A, a muffler 20 to be tested is inserted into the first pipe 1 and the second pipe 2 of the apparatus for measuring loss of sound traveled in a muffler of an automobile. The muffler 20 has flanges 21 and 22 at both ends respectively and its flanges are fastened to flanges $1a$ and $2a$ of the pipes 1 and 2 respectively by bolts. In this manner, the muffler is mounted to the apparatus for measuring a loss of sound traveled in a muffler of an automobile and the flanges are sealed such that the sound does not leak out. To do this, rubber pads 12 are inserted into the connecting portions between the flanges of the muffler 20 and the flanges $1a$ and $2a$ of the pipes respectively as shown in FIGS. 1B and 1C. (In these figures, flange $1a$ only is shown.)

Figure 2:
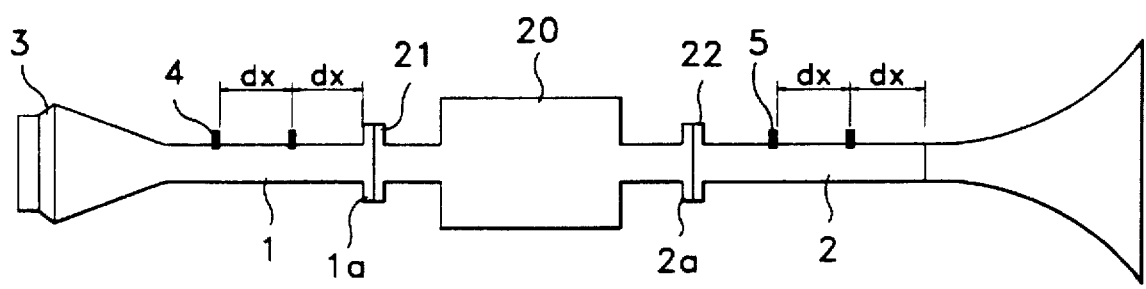
FIG. 2 shows a mounting location of the microphone used in the apparatus for measuring a loss of sound traveled in a muffler of an automobile according to the present invention.

FIG. 2 shows a mounting location of the microphone used in the apparatus for measuring a loss of sound traveled in a muffler of an automobile according to the present invention.

As shown in FIG. 2, a sound source 3 such as a speaker is provided at the end of the first pipe 1 opposed to the end connected to the muffler 20 to produce a sound into the pipes 1 and 2. Although a speaker is used as a sound source in the present embodiment, other sound sources can be used.

Before the sound produced from the sound source 3 passes through the muffler 20, the level of sound is measured by the first multiple microphones 4 mounted at the first pipe 1. It is preferable that the number of the first microphones be two.

The sound passes from the first pipe 1 to the muffler 20 and the level of sound is reduced in the muffler 20. The sound then travels into the second pipe 2 and the level of sound is measured by the second multiple microphones 5 mounted at the pipe 2. The number of the second microphones is preferably two.

In the meanwhile, an available frequency range is 50 to 2000 Hz according to the size of diameter for the inlet $20a$ and outlet $20b$ of the muffler 20 as shown in FIG. 1. When the diameter of the inlet $20a$ and outlet $20b$ is indicated "D", the plane wave region obtained from the microphone 4 and 5 mounted at the pipe 1 and 2 respectively is as follows;

$$f\text{cutoff} = \frac{\lambda nmC}{\pi D}$$

wherein $\lambda nm$ is provided that the first differential of Bessel function is zero and C is a velocity of sound. At room temperature of 27° C., $\lambda nm=1.84$ and $C=343$ m/s. If D=49 mm, then $$f\text{cutoff} = \frac{1.84 \times 343}{\pi \times 0.049} \cong 4100 \text{(Hz)}$$

Because the available frequency range is 50 to 2000 Hz, the actually measured maximum frequency is to be 2000 Hz.

By using the maximum frequency, the distance between of the microphones 4 or 5 mounted at the pipe 1 or 2 is decided. The distance is decided by the following equation;

$$\Delta x = \frac{C}{2f\max}$$

According to the above equation, the distance $\Delta x<85.7$ mm so $\Delta x$ is decided to 60 to 80. The distance $\Delta x$ may be smaller than the above value but it is preferable to decide a larger value considering reducing of random error effect which is larger when wave length is larger.

The microphone 4 or 5 is located at a distance $\Delta x$ from the end of the pipe 1 or 2 connected to the muffler 20 and an additional microphone 4 or 5 is located at a distance $\Delta x$ from the previously mounted microphone 4 or 5.

It is preferable to use the microphone 4 or 5 each of which has substantially the same responding characteristics (size and phase). Also, it is preferable that the microphones 4 and 5 are mounted together for measuring. In case that each one of microphones 4 and 5 is the first and second pipes 1 and 2, each one of mounting holes is formed at the first and second pipes 1 and 2. Otherwise, in case that multiple mounting holes are formed at the first and second pipes 1 and 2, the mounting holes except for that used should be sealed to prevent the sound not to leak out.

Figure 3:
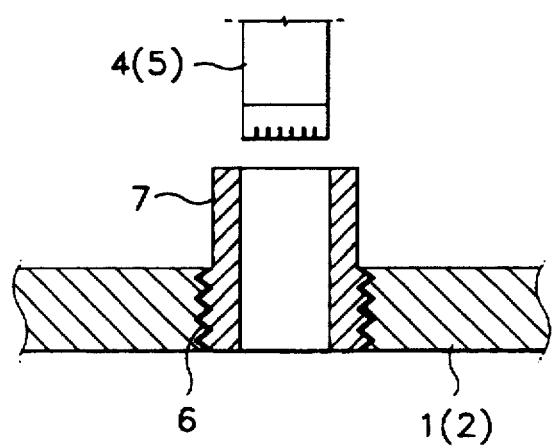
FIG. 3 shows the mounting status of the microphone of FIG. 2 in detailed.

FIG. 3 shows in detail the microphone 4 and 5 mounted at the first and second pipes 1 and 2. As shown in FIG. 3, each of the microphone 4 and 5 is inserted into a jig 7 and the jig is fastened to a screw hole 6 formed at the first and second pipes 1 and 2. At this time, the microphone 4 or 5 is secured carefully and sealed to prevent both sound leakage and jamming within the jig 7.

Figure 4:
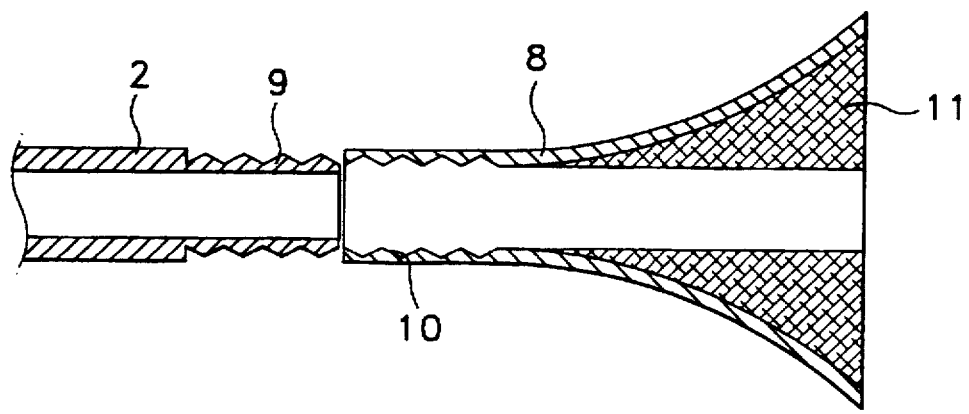
FIG. 4 shows a non-reflect device of the apparatus for measuring the loss of sound traveled in a muffler of an automobile of FIG. 2.

FIG. 4 shows a non-reflect device of the apparatus for measuring loss of sound traveled in a muffler of an automobile of FIG. 2. The non-reflect device 8 has recesses 10 at the inner surface of its end and the end 9 of the second pipe 2 is inserted into the recesses 10 of the non-reflect device to mount the non-reflect device to the second pipe 2.

The sound passes through the first and second pipes 1 and 2 and enters into the non-reflect device 8 without returning from the second pipe end 9 to the first and second pipes 1 and 2. Although the non-reflect device 8 is connected to the second pipe 2 by push insertion as described above, it can be connected and sealed in other manners, for example flange engagement or screw engagement.

The non-reflect device 8 has an enlarged end and a sound absorber 11, for example glass wool is filled in the inner of the enlarged end to prevent sound reflecting. The enlarged end of the non-reflect device 8 has a curvature of $2 \ast r_o \ast e^{\alpha x}$; wherein $r_o$ is a radius of the non-reflect device and e is indicated to exponential and x is a length of the non-reflect device. If $\alpha$ is smaller and x is longer, good characteristics are obtained.

The sound absorber 11 is supported by a hollow net to make good sound path in the center of the non-reflect device and it is wrapped by a cloth so glass wool does not leak out.

Figure 5:
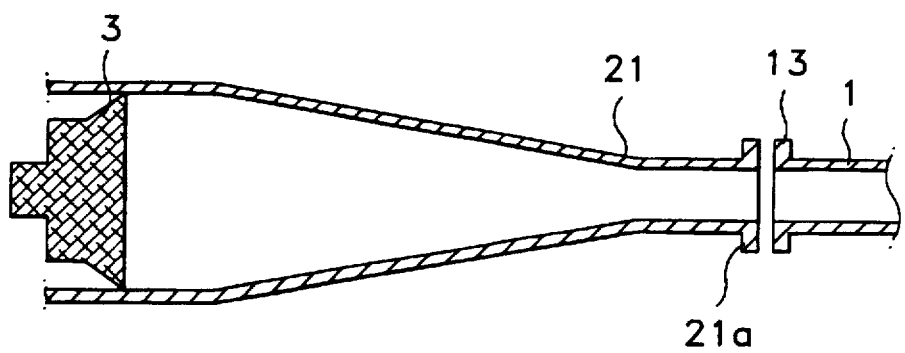
FIG. 5 shows a sound source of the apparatus for measuring loss of sound in a muffler of an automobile of FIG. 2.

FIG. 5 shows a sound source of the apparatus for measuring loss of sound traveled in a muffler of an automobile of FIG. 2. As shown in this figure, a sound source 3 is a speaker or horn driver and the front of the sound source is received into the enlarged end of converging pipe 21. The other end $21a$ of the converging pipe 21 is connected to the end 13 of the first pipe 1.

It is preferable that the sound source has a large output so it outputs a relative plane wave in a frequency domain to be tested. Normally, the horn driver is selected as a speaker of good low frequency ability so it outputs a signal below or equal to 100 Hz. The sound source 3 also is sealed to the pipe to prevent sound leakage.

The operating manner of sound source 3 are two kinds; one type is white noise and other type is sinesweep. The sinesweep type has an advantage of increasing a ratio of S/N but has a drawback of longer measuring time.

Figure 6:
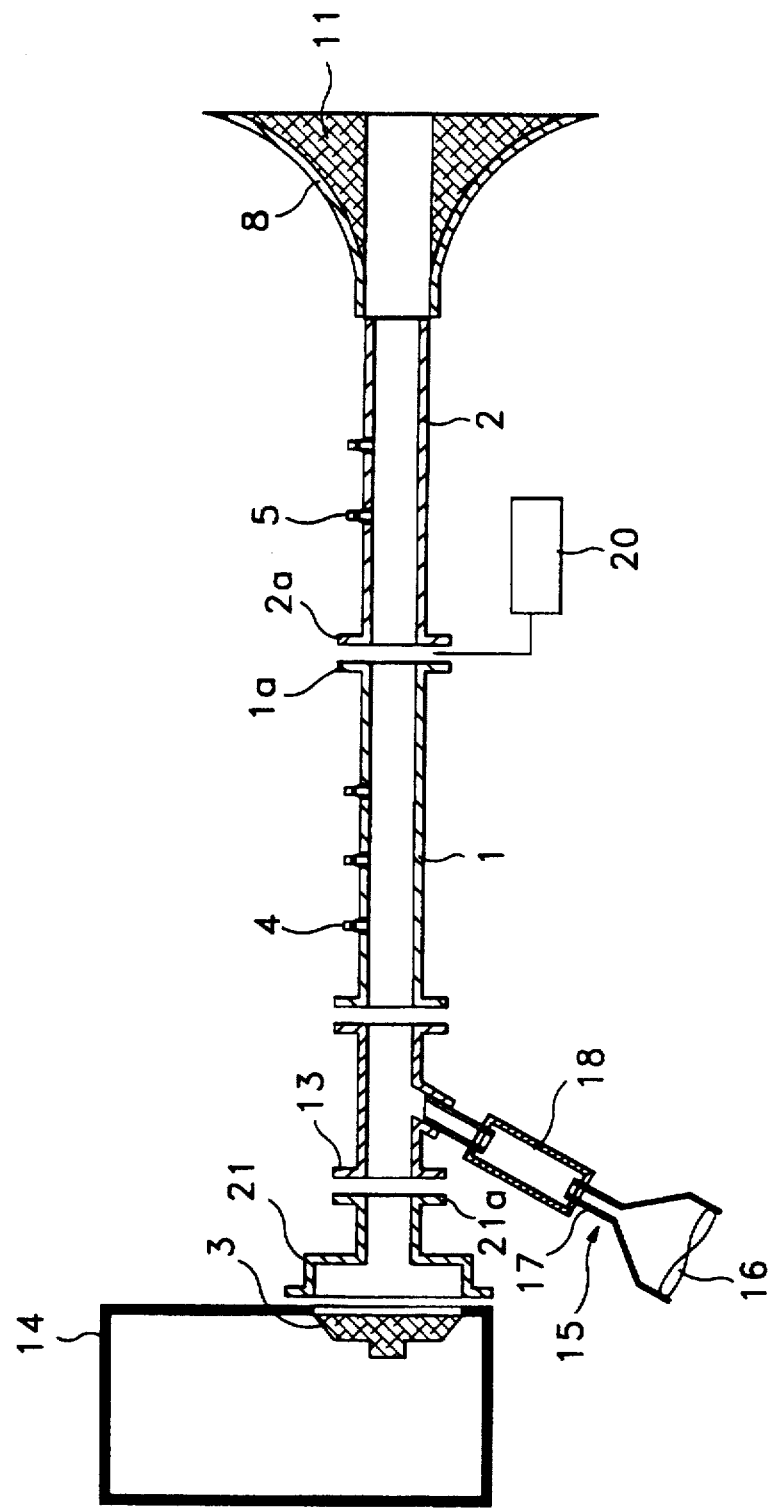
FIG. 6 shows an overall construction of the apparatus for measuring loss of the sound traveled in a muffler of an automobile.

To enhance an efficiency of sound source, the sound source 3 is received preferably into a insulating chamber 14 as shown in FIG. 6 so an external noise can be insulated. Also, the sound source 3 is located better at the upper portion than at the center portion of the insulating chamber 14 and its proper location is at 2:3 or 1:2 in height of the chamber.

FIG. 6 shows an overall construction of the apparatus for measuring loss of sound traveled in a muffler of an automobile. As shown in this figure, in the present invention, a flow creating device 15 is provided at the first pipe 1 in order for the sound created by the sound source 3 to rapidly pass through the first and second pipe 1 and 2.

The flow creating device 15 comprises a fan 16 operated by a motor(not shown), a guide pipe 17 connected to the first pipe 1 to guide the air flow created by the fan 16 to the first pipe 1, a fan muffler 18 provided at the middle portion of the guide pipe 17 to eliminate the noise created by the operation of the fan 16 and a flow rate sensor.

The flow creating device 15 is attached to the first pipe 1 in angular position to direct the air flow created by the fan 16 in the direction of sound propagation to aid the sound propagation. Considering the actual exhaust condition for automobile, the flow creating device, for example, fan or compressor is required and the regulating mean, i.e. regulator and the flow rate sensor are also required. The flow rate sensor(not shown) is mounted at the first and second pipe 1 and 2 by a jig as the same as that used for the microphone. The flow creating device is preferable to create low noise and vibration. The fan is operated by an additional power regulating device and it is preferable to record the relative table of the current and flow rate.

The fan muffler 18 is provided to eliminate the noise created by the flow creating device 15 and the specification of the fan muffler 18 is decided by the following equation;

$$TL=10 \log_{10}(1+(M-1/M)^2/4 * \sin^2 Kl)$$

wherein M is a sectional ratio of the guide pipe 17 and the fan muffler 18,

K is weber coefficient, $K=\omega/c=2 f/c$, l is a length of the fan muffler 18.

The above equation is a function of frequency so a resonance point is considered.

In the meantime, the fan 16 is used to have a large capacity so it can create an air flow of mach number 1.3.

In accordance with the apparatus for measuring a loss of sound traveled in a muffler of an automobile mentioned above, the levels of sound before and after the muffler can be accurately measured so a loss of sound passing through the muffler is measured in accurate value thereby obtaining the muffler of automobile of good sound eliminating ability.

Although the preferred embodiment of the present invention has been disclosed for illustrative purpose, those skilled in the art will appreciate that various modifications, additions and substitutions are possible, without departing from the scope and spirit of the present invention as disclosed in the accompanying claims.

What is claimed is:

1. An apparatus for measuring a loss of sound traveled in a muffler of an automobile, comprising:

a first pipe and a second pipe between which is inserted the muffler to be tested;

a sound source connected to one end of the first pipe opposite to the muffler to create a sound into the first and second pipes, first microphones mounted at the first pipe to measure the level of sound before the sound reaches the muffler, second microphones mounted at the second pipe to measure the level of sound after exiting the muffler; and a non-reflecting means connected to the second pipe for preventing reflection of the sound back into the first and second pipes.

2. The apparatus as claimed in claim 1, further comprising a flow creating device for providing an air flow in the first pipe to thereby aid in sound propagation of the sound generated from the sound source into the first and second pipes.

3. The apparatus as claimed in claim 1, wherein one of said first microphones is located at a first distance from the end of said first pipe connected to the muffler, and another of said first microphones is located at said first distance from said one of said first microphones.

4. The apparatus as claimed in claim 1, wherein each of the first and second microphones is respectively inserted into a jig fastened to a screw hole formed at the first and second pipes.

5. The apparatus as claimed in claim 1, wherein the non-reflection means is a non-reflect device having an enlarged end, and further including a sound absorber material filling the device prevent sound from reflecting.

6. The apparatus as claimed in claim 2, wherein the flow creating device comprises a fan operated by a motor, a guide pipe connected to the first pipe to guide the air flow created by the fan to the first pipe, a fan muffler provided at the middle portion of the guide pipe to eliminate the noise created by the operation of the fan and a flow rate sensor.

7. The apparatus as claimed in claim 6, wherein the specification of the fan muffler is decided by the following equation;

$$TO=10 \log_{10}(1+(M-1/M)^2/4 * \sin^2 Kl)$$

wherein M is a sectional ratio of the guide pipe and the fan muffler,

K is weber coefficient, $K=\omega/c=2 f/c$, l is a length of the fan muffler.

* * * * *